United States Patent
Doerr et al.

(10) Patent No.: US 9,364,663 B2
(45) Date of Patent: Jun. 14, 2016

(54) DETECTOR FOR ELECTROMAGNETIC FIELDS

(71) Applicant: BIOTRONIK SE & Co. KG, Berlin (DE)

(72) Inventors: Thomas Doerr, Berlin (DE); Ingo Weiss, Berlin (DE); Steffen Kibbel, Berlin (DE)

(73) Assignee: BIOTRONIK SE & Co. KG, Berlin (DE)

( * ) Notice: Subject to any disclaimer, the term of this patent is extended or adjusted under 35 U.S.C. 154(b) by 0 days.

(21) Appl. No.: 14/697,062

(22) Filed: Apr. 27, 2015

(65) Prior Publication Data

US 2015/0352354 A1    Dec. 10, 2015

Related U.S. Application Data

(60) Provisional application No. 62/007,953, filed on Jun. 5, 2014.

(51) Int. Cl.
| | |
|---|---|
| *A61N 1/00* | (2006.01) |
| *A61N 1/08* | (2006.01) |
| *A61N 1/39* | (2006.01) |
| *A61N 1/37* | (2006.01) |
| *G01R 33/022* | (2006.01) |
| *G01R 33/28* | (2006.01) |

(52) U.S. Cl.
CPC ............... *A61N 1/08* (2013.01); *A61N 1/3718* (2013.01); *A61N 1/3931* (2013.01); *G01R 33/022* (2013.01); *G01R 33/285* (2013.01); *G01R 33/288* (2013.01)

(58) Field of Classification Search
CPC ..... A61N 1/08; A61N 1/3718; A61N 1/3931; G01R 33/022; G01R 33/24; G01R 33/285; G01R 33/288
See application file for complete search history.

(56) References Cited

U.S. PATENT DOCUMENTS

| | | | |
|---|---|---|---|
| 6,101,417 | A | 8/2000 | Vogel et al. |
| 6,522,920 | B2 | 2/2003 | Silvian et al. |
| 7,509,167 | B2 | 3/2009 | Stessman |
| 8,768,430 | B2 | 7/2014 | Doerr et al. |
| 2006/0293591 | A1 | 12/2006 | Wahlstrand et al. |

(Continued)

FOREIGN PATENT DOCUMENTS

EP    2338414 A1    6/2011

OTHER PUBLICATIONS

European Search Report received from EP Application Serial No. 15164573.6-1652, dated Oct. 9, 2015, 7 pages.

*Primary Examiner* — George Manuel
(74) *Attorney, Agent, or Firm* — Arc IP Law, PC; Joseph J. Mayo

(57) ABSTRACT

An implantable medical device (IMD) including a power supply, a sensing device and/or a stimulation device, a control unit, a magnetic resonance (MR) detection unit, and at least two magnetic field sensors. The power supply is connected to one or more of the sensing device, the stimulation device, the control unit, the MR detection unit and the magnetic field sensors. The control unit is connected to the sensing device and/or stimulation device, to the MR detection unit, and to the at least two magnetic field sensors. The at least two magnetic field sensors are arranged spatially separately from one another and the MR detection unit determines a spatial and/or temporal gradient of magnetic field strengths detected by the at least two magnetic field sensors and transmitted to the MR detection unit. The MR detection unit detects an MR field and transmits an MR signal to the control unit.

9 Claims, 4 Drawing Sheets

(56) References Cited

U.S. PATENT DOCUMENTS

| | | |
|---|---|---|
| 2008/0071168 A1 | 3/2008 | Gauglitz et al. |
| 2009/0138058 A1* | 5/2009 | Cooke et al. ................ 607/5 |
| 2010/0176808 A1 | 7/2010 | Legay |
| 2011/0092802 A1 | 4/2011 | Steckner |
| 2011/0137359 A1 | 6/2011 | Stubbs et al. |
| 2012/0194191 A1 | 8/2012 | Jenison |
| 2013/0289384 A1 | 10/2013 | Jenison et al. |

* cited by examiner

DETECTOR FOR ELECTROMAGNETIC FIELDS

BACKGROUND OF THE INVENTION

1. Field of the Invention

Embodiments of the invention generally relate to a method for identifying electromagnetic fields with implantable medical devices, specifically electromagnetic fields that occur when using nuclear magnetic resonance imaging and tomography (e.g., MRI, MRT) devices.

2. Description of the Related Art

Although magnetic resonance (MR), magnetic resonance imaging (MRI) and magnetic resonance tomography (MRT) examinations (hereinafter collectively referred to as MR) are generally becoming ever more significant in diagnostic medicine, MR examinations are contraindicated for some patients. Typically, such a contraindication may be caused by an active implanted medical device.

Generally, besides possible heating effects of implants, particularly with small conductive structures, other problems include erroneous identifications of events in the heart, such as, but not exclusively, ventricular fibrillation, or fast cardiac dysrhythmia, (VF) and the high static magnetic fields and resultant magnetizations of electric components. The above-mentioned effects typically occur particularly with active implants, such as, but not exclusively, defibrillators/cardioverters (ICDs), pacemakers, cardiac resynchronization devices, neurostimulators or drugs pumps, but also with passive implants, such as monitoring devices. However, generally, the function of other implanted medical devices may also be disturbed by electromagnetic fields, and these devices must not be operated in environments subject to increased electromagnetic loads. The following prior art concerns, in particular, the problem of detecting electromagnetic interference fields in the presence of implanted medical devices (IMDs).

U.S. Pat. No. 6,522,920 to Silvian et al., entitled "System and Method of Protecting Transformer-Driven Switches from External Magnetic Fields", describes a system for protecting the inductively actuated high-voltage switch of an ICD during shock delivery in a magnetic field. In Silvian et al., the system monitors whether a sufficient gate voltage is provided at the moment of the shock delivery. According to Silvian et al., the monitoring is assessed by means of an assessment of the secondary voltage of the inductive drivers.

For example, United States Patent Publication 20080071168, to Gauglitz et al., entitled "Systems and Methods for Sensing External Magnetic Fields in Implantable Medical Devices", provides an impedance measuring unit and an RLC member for detection of a magnetic field and to perform the detection by determining the inductance in the RLC component. Typically, an additional or adapted impedance measuring unit is required for this purpose.

U.S. Pat. No. 7,509,167 to Stessman, entitled "MRI Detector for Implantable Medical Device", describes the identification of a magnetic field by the measurement of the timings for the actuation of the high-voltage transformer of the primary side or alternatively by the measurement of peak currents during a charging cycle. For example, the disadvantages of the described system of Stessman are that the measurement of the timings has to be very quick (us to ns), and that a direct current measurement may only be implemented with difficulty due to the necessary measuring resistor, which would lengthen the charge times for the high-voltage capacitor.

Furthermore, U.S. Pat. No. 6,101,417, to Vogel et al., entitled "Implantable Electrical Device Incorporating a Magnetoresistive Magnetic Field Sensor", appears to describe the use of a giant magnetoresistive ratio (GMR) sensor instead of a reed switch, however not for detection of MR fields, rather for activation of a magnet mode in the implant.

Generally, the technical solutions provided in the prior art above, for detecting electromagnetic interference fields with implanted medical devices, include uncertainties regarding the sensitivity or specificity, or such solutions are not efficient enough.

Therefore, in view of the above, there is a need for an efficient and reliable detector for electromagnetic fields for MR detection.

BRIEF SUMMARY OF THE INVENTION

One or more embodiments of the invention include an implantable medical device (IMD).

In at least one embodiment of the invention, the IMD includes at least one power supply, one or more of at least one sensing device and at least one stimulation device, at least one control unit, at least one MR detection unit, and at least two magnetic field sensors. In one or more embodiments, the at least one power supply may be connected directly or indirectly to one or more of the at least one sensing device, the at least one stimulation device, the at least one control unit, the at least one MR detection unit and the at least two magnetic field sensors. In at least one embodiment, the at least one control unit may be connected directly or indirectly to one or more of the at least one sensing device and the at least one stimulation device. In one or more embodiments, the at least one control unit may be connected directly or indirectly to the at least one MR detection unit and to the at least one magnetic field sensor. According to at least one embodiment, the at least two magnetic field sensors may be arranged spatially separately from one another. In one or more embodiments, the at least one MR detection unit may determine a spatial and/or temporal gradient of magnetic field strengths, wherein the magnetic field strengths are detected by the at least two magnetic field sensors and transmitted to the at least one MR detection unit. In at least one embodiment, the at least one MR detection unit may detect an MR field and transmit an MR signal to the at least one control unit if either

- at least one magnetic field strength of the magnetic field strengths detected by the at least two magnetic field sensors is above a first predetermined threshold value, or
- the magnetic field strengths detected by the at least two magnetic field sensors are below the first predetermined threshold value and above a second predetermined threshold value, and the spatial and/or temporal gradients of the magnetic field strengths lie in a first predetermined range of threshold values.

By way of at least one embodiment, the gradient may indicate a change of a magnetic field in space or in time, wherein the detection with the at least two magnetic field sensors provided in the IMD may be determined via a variation of the measured magnetic field strengths over time, wherein the at least two magnetic field sensors are arranged rigidly in the respective IMD or in an electrode line.

In one or more embodiments, the term MR field includes the electromagnetic field of an MR device. In at least one embodiment, a static magnetic field of an MR or MRI device is used, wherein the static magnetic field is particularly strong.

In one or more embodiments, each magnetic field sensor of the at least two magnetic field sensors may include a GMR sensor, a Hall sensor, a reed switch, a MagFET, or any combination thereof, or any another magnetic field sensor within the field of the invention.

In at least one embodiment, the at least one control unit may change into a predetermined operating mode in response to the MR signal of the at least one MR detection unit. In one or more embodiments, the predetermined operating mode may be an MR-safe state or an MR mode.

By way of at least one embodiment, the IMD may include an implantable pacemaker and/or a defibrillator/cardioverter (ICD), or may include a cardiac resynchronization IMD with an ICD and/or pacemaker.

In at least one embodiment, the IMD may include a neurostimulator or a drug pump.

According to one or more embodiments, an MR-safe state may include a suppression of delivery of high-voltage shocks and/or provision of alternative IMD modes. For example, in at least one embodiment, an MR-safe state may include temporary switch-off of the IMD function, such as suppression of the delivery of IMD stimulations, or may include the switchover into an asynchronous stimulation mode, such as delivery of IMD stimulations without consideration and/or detection of rhythms naturally produced naturally in a body.

In one or more embodiments, a decision regarding a suitable MR-safe state may be made either when programming the IMD, or automatically when programming the IMD, or automatically during the detection of an MR field, or automatically at predetermined moments in time, or with certain events or patient states. In at least one embodiment, the IMD may be switched into an MR-safe state (MR mode) by programming or by remote programming.

In one or more embodiments of the invention, the predetermined operating mode includes parameters that may be predetermined in accordance with one or more of the magnetic field strengths determined by the at least one MR detection unit, the temporal gradient fields and/or spatial gradient fields.

By way of at least one embodiment, the at least one MR detection unit may evaluate the gradient and absolute value of the detected magnetic field strengths when the detected magnetic field strengths lie below the first predetermined threshold value.

In one or more embodiments, the at least two magnetic field sensors may be arranged within the IMD or at least one of the magnetic field sensors may be arranged within the IMD and at least one further magnetic field sensor may be arranged in an electrode line connected to the IMD. In at least one embodiment, an electrode line may be one or more of a line that applies electronic pulses and a sensor line. In one more embodiments including a sensor line, the respective sensor may be connected electronically, optically or optoelectronically to the IMD.

In one or more embodiments using a drug pump, the electrode line may be one or more of a hollow line to apply drugs and a sensor line.

In at least one embodiment, the at least one MR detection unit may form a signed difference between the at least two magnetic field sensors, and may use different first predetermined threshold values and/or second predetermined threshold values and/or first predetermined range of threshold values, depending on the sign, to detect the MR field.

In one or more embodiments, the minimum distance between the at least two magnetic field sensors is selected in accordance with a resolution of the at least two magnetic field sensors, such that the resolution is sufficient to distinguish between a local magnetic field and a widely distributed MR field with reference to the spatial gradients. In at least one embodiment, a local magnetic field may include magnetic fields of permanent magnets or electromagnets as are present in a patient environment (for example in the form of loudspeakers or simple permanent magnets). In one or more embodiments, the widely distributed MR fields differ from the local fields by their size. In at least one embodiment, the magnetic fields may thus extend about 100-150 cm beyond the MR device with significantly measurable field strength of more than 2 mT, wherein 2 mT is a response threshold of the reed switch in conventional cardiac pacemakers. By contrast, typical magnetic fields to be expected in the patient environment achieve a propagation of a few centimeters within such a field strength.

In one or more embodiments, the MR signal may be transmitted to the at least one control unit and the at least one control unit may cause at least one predetermined automatic switchover of at least one implant setting of the IMD.

In at least one embodiment, the IMD may include one or more of at least one elongate electrode line and at least one sensor line.

It one or more embodiments, the at least one MR detection unit may identify an MR-typical journey of an IMD on a patient bed, based on one or more of a change over time of the measured values of the at least two magnetic field sensors and a difference between the measured values of the at least two magnetic field sensors. In one or more embodiments, an MR-typical journey may include the entry or the exit of the patient bed into or out of the MR device or MRI device, with a patient having an IMD. In an MR-typical journey, in at least one embodiment, the patient may be brought at speed into or out of a scanning position of the respective MR device, thus enabling determination of a change in the magnetic field strengths.

In at least one embodiment of the invention, predetermined or predeterminable parameters and/or threshold values and/or settings (such as settings for an MR-safe state, an MR mode or a predetermined operating mode) may be set, changed or predetermined, or any combination thereof, via one or more of a local programming device and remote programming.

In one or more embodiments, "remote programming" may include the programming of an IMD, wherein the IMD and a programming unit or a programming end may be spatially separated from one another, such that near-field telemetry (for example <10 m) typically present is not sufficient alone to bridge the spatial separation.

In at least one embodiment, a switch-on of the MR-safe sate or when the MR-safe state has been switched on may be transmitted using telemetric remote monitoring, such as a home monitoring system. As such, in one or more embodiments, when the MR-safe state is switched on, a signal or information is sent directly or via at least one intermediate device, for example a patient device, to a central unit, wherein the central unit processes the information or the signal or forwards it on where necessary. In one or more embodiments, if, when the MR-safe state is switched on, there is no connection to the central unit or it is not possible to establish such a connection, the information or the signal may be sent or transmitted at a later moment in time, for example as soon as there is a connection to the central unit or when such a connection may be produced.

In at least one embodiment, telemetric remote monitoring may include wherein information or signals may be transmitted from an IMD to a spatially distanced unit in order to enable a monitoring of the patient, even without a doctor's visit or hospitalization, for example, in that data may be transmitted from the IMD via a service center to a responsible doctor. In one or more embodiments, data may also be transmitted via the service center to the IMD.

One or more embodiments of the invention may include a combination of methods for detecting electromagnetic fields, especially MR fields, and in combination with different responses to electromagnetic fields, especially MR fields. In at least one embodiment of the invention, further detection methods may include one or more of:

GMR sensors, monitoring of a battery voltage when charging a capacitor, in particular a high-voltage capacitor, MagFETs, evaluation of induced currents in electrodes or antennas as an indicator, detection of specific vibrations or components, such as sensors that detect vibrations induced by Lorentz forces as an indicator, and position sensors as one or more indicators.

In one or more embodiments, indicators may include methods and/or devices that determine whether electromagnetic interference fields are present.

At least one embodiment of the invention may include other responses as further responses to detected electromagnetic fields, especially MR fields, such as, but not limited to, one or more of remaining for a prolonged period of time in an MR-safe state or a state that is insensitive to electromagnetic interference fields, synchronizing electrical measurements (for example impedance measurements) with use of field strength minimum values that occur with periodic or pulsed electromagnetic fields, or synchronizing a stimulation using the field strength minimum values, and emitting electromagnetic pulses to signal, for example to an MR device, that a medical device, such as an implant, is present in the electromagnetic field, and may include transferring information by emitting electromagnetic pulses, in addition to the interference, and displaying the information on the screen of the MR device.

One or more embodiments of the invention may include a position sensor to check plausibility, and to check if positive identification of MR is only given when the position sensor signals a prone posture and/or another presettable posture.

At least one embodiment of the invention may include the combination of the position sensor with the identification of an MR-typical journey of an IMD on the patient bed, wherein such a combination provides a particularly high sensitivity for the identification of MR fields of MR devices.

In one or more embodiments, the position sensor may be self-calibrating, wherein the calibration takes place under presettable marginal conditions, such as, but not limited to, one or more of time of day, heart rate, breathing rate, hemodynamic parameters, and activity (such as using a motion sensor).

BRIEF DESCRIPTION OF THE DRAWINGS

The above and other aspects, features and advantages of at least one embodiment of the invention will be more apparent from the following more particular description thereof, presented in conjunction with the following drawings, wherein.

DETAILED DESCRIPTION OF THE INVENTION

The following description is of the best mode presently contemplated for carrying out at least one embodiment of the invention. This description is not to be taken in a limiting sense, but is made merely for the purpose of describing the general principles of the invention. The scope of the invention should be determined with reference to the claims.

Figure 1:
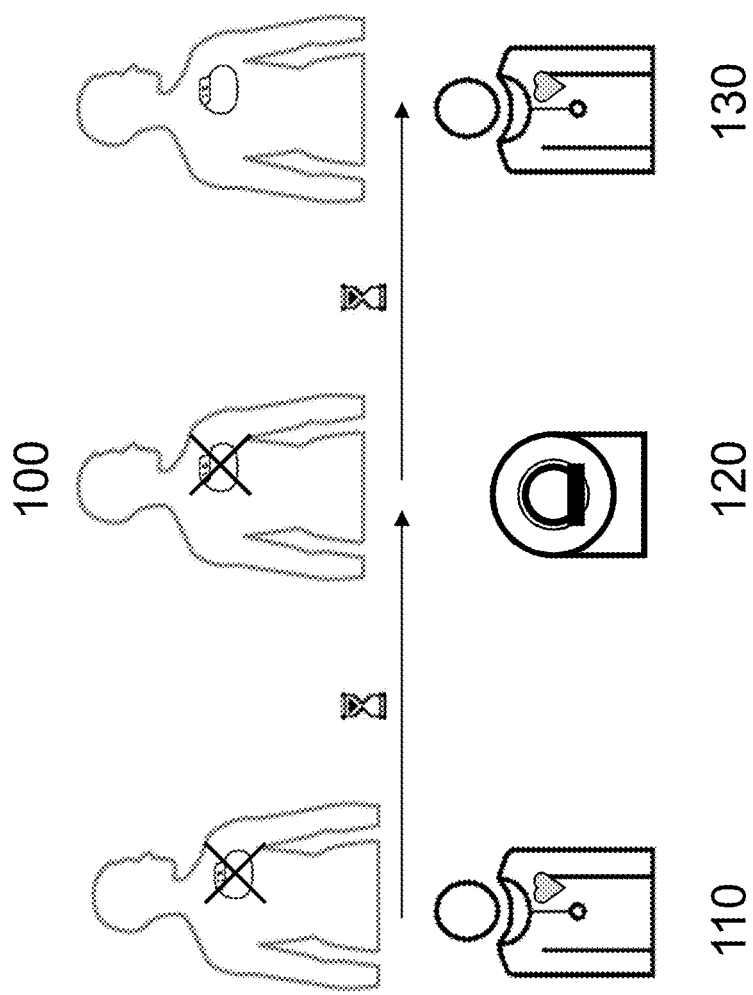
FIG. 1 shows a schematic illustration of a course of an MR examination.

FIG. 1 shows a schematic illustration of a course of a typical MR examination with an MR-compatible ICD. As shown in FIG. 1, an ICD patient (100) may have an aftercare consultation with a cardiologist before the planned MRT examination, wherein the ICD is switched off (110) in order to rule out an inadequate shock delivery during the MR scan by oversensing caused by the electromagnetic alternating fields acting on the electrode line. As shown in FIG. 1, the MRT examination may be carried out by a radiologist after a temporal delay lasting from hours to days (120). After a further delay, the patient may again be treated by the cardiologist (130) and the ICD may be switched back on. During the entire period from (110) to (130), the patient is without the protection of the implanted defibrillator and may be without rhythm monitoring. The remaining residual risk, for example, which may be measured in proportion to the benefit of the MRT examination, is generally accepted.

Typically, financial and logistical outlay of such a procedure is also generally very high and in many cases rules out the emergency use of MRT.

Figure 2:
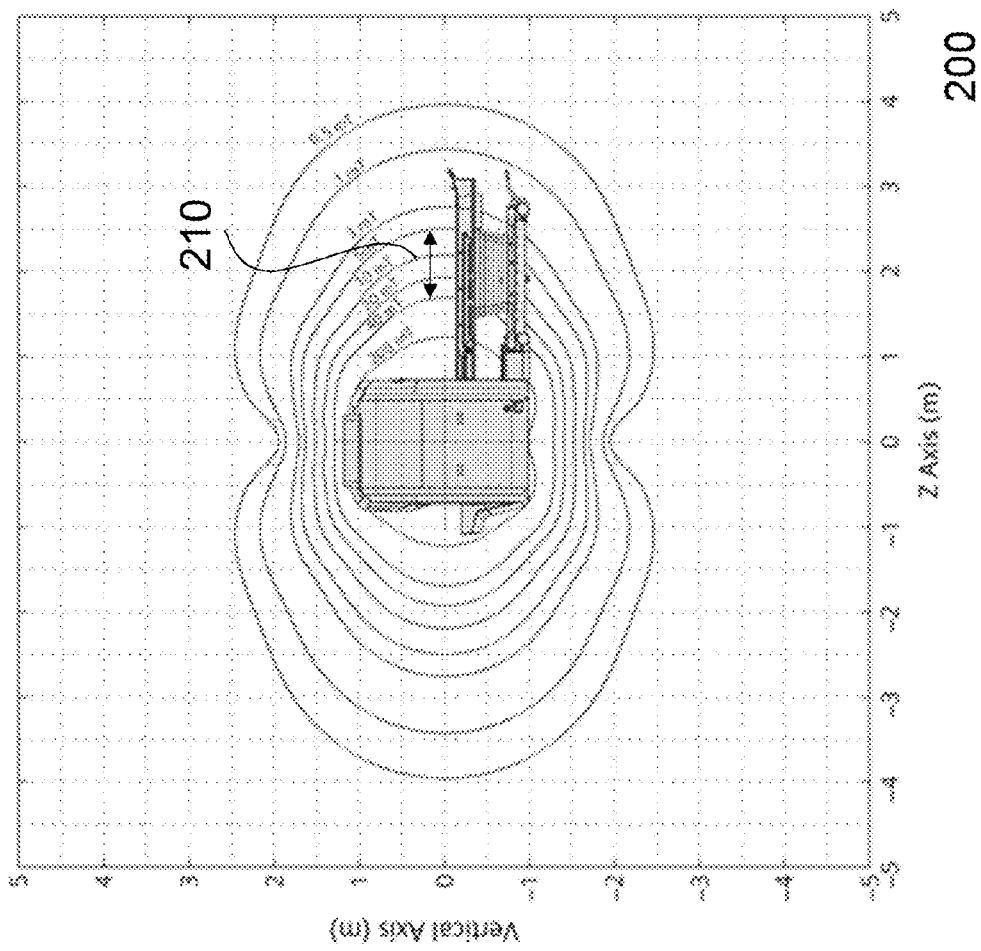
FIG. 2 shows a schematic illustration of a course of an MR B0 field.

FIG. 2 shows a schematic illustration of a course of an MR B0 field, and the problem with using an individual magnetic field sensor for MRT identification. In FIG. 2, the field strength distribution of the B0 field of an MR device beyond the scanner is plotted by way of example (200). As shown in FIG. 2, during an MR scan of a patient with the feet of the patient in the isocenter, the magnetic field strengths may fall to approximately 5 mT at the head end of the patient, such that a magnetic field sensor in an implant in the vicinity of the head cannot perceive any MR-typical magnetic field strengths, and thus does not perform an automatic MR switchover. As such, the implant would generally be located at a corresponding distance from the magnet of the MR device.

Generally, the MR-typical magnetic field distribution differs considerably in terms of its "size" from that of a "normal" magnetic field source to be expected in the patient environment, for example a magnet in a programmer head. As such, the field strengths above 2 mT may achieve a propagation of a few centimeters (typically <10 cm).

Figure 3:
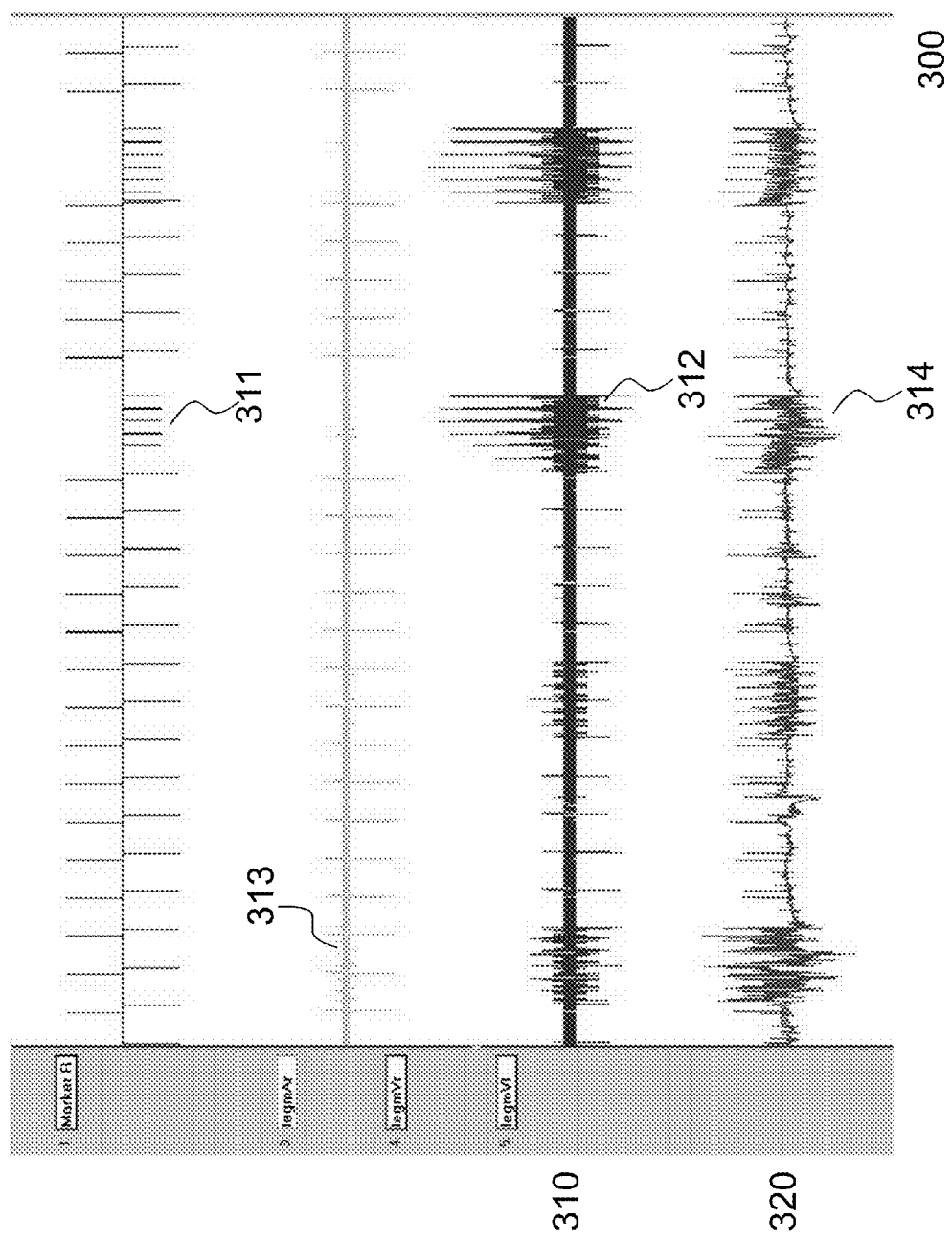
FIG. 3 shows a schematic illustration of an oversensing in MRT.

FIG. 3 shows a schematic illustration of an oversensing in MRT, wherein a measurement (300) is performed with an ICD system in a position of a patient with the feet in the isocenter and an implant in a chest region (210) of the patient (as shown in FIG. 2). As shown in FIG. 3, an oversensing (310, 320) is distinct in the ventricular sensing channels, which may lead to, in using an undeactivated ICD, to an inadequate shock therapy. Such oversensing is shown in the marker channel at fast right-ventricular detection markers (311), which are perceived by the implant following the distinct MR interference (312) above a threshold value. If the number of fast detection markers (311) exceeds a programmable limit value, an ICD may inadequately introduce an antitachycardia therapy.

As shown in FIG. 3, comparable interferences may also be seen in the right-atrial sensing channel (313) and in the left-ventricular sensing channel (314). In the right-atrial sensing channel (313) and in the left-ventricular sensing channel (314), however, the interference amplitudes have not yet reached the programmed sensing thresholds, and therefore incorrect detection markers may be avoided.

With such oversensing, the magnetic field to be measured at the implant is only approximately 30 mT.

Figure 4:
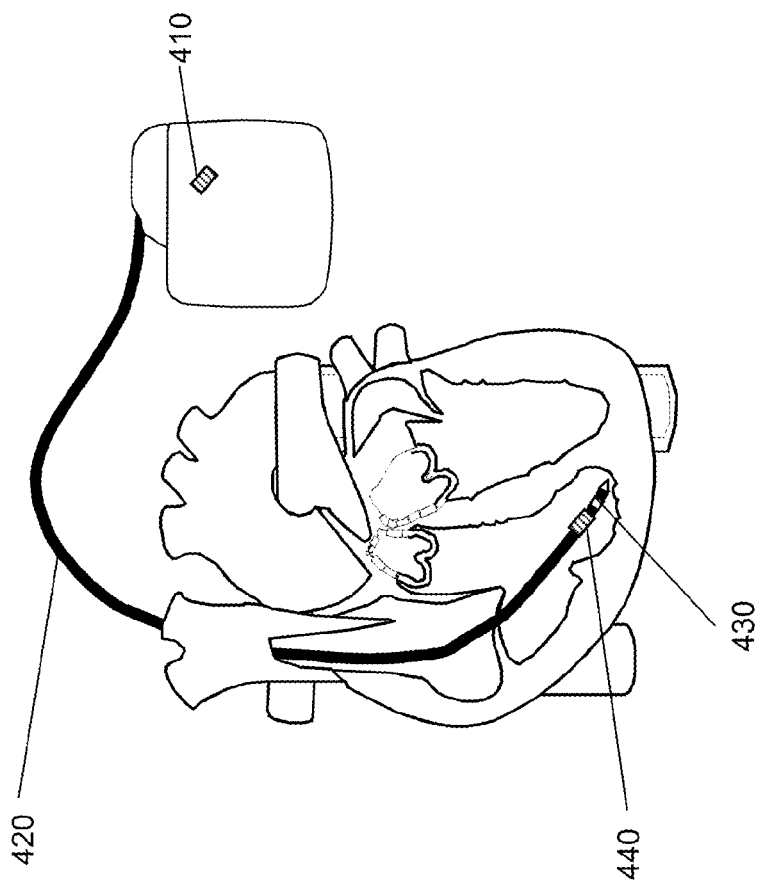
FIG. 4 shows a schematic illustration of an IMD with a two-magnetic field sensor system; according to one or more embodiments of the invention.

FIG. 4 shows an IMD system with two magnetic field sensors, according to one or more embodiments of the invention. In at least one embodiment, implantable medical device (IMD), such as a cardiac pacemaker, includes a first magnetic field sensor (410). In one or more embodiments, the implant may be connected to an electrode line (420), which senses and stimulates the heart via a distal dipole (430). In order to identify the spatial propagation of a magnetic field, by way of at least one embodiment, the electrode line (420) includes a further magnetic field sensor (440), of which the measured values may be queried by the IMD.

According to one or more embodiments, when the first magnetic field sensor (410) senses a magnetic field above a threshold, the second magnetic field sensor (440) is queried, and an MRT switchover may then occur if the second magnetic field sensor (440) also indicates a magnetic field above the threshold. In at least one embodiment of the invention, the threshold of the second magnetic field sensor (440) may be derived from a measured magnetic field of the first magnetic field sensor (410), and magnetic field propagations to be expected with MRT are set accordingly. In one or more embodiments, a reliable distinction between local magnetic fields, such as patient magnets, or MR-typical magnetic fields beyond the scanner may be made.

In at least one embodiment, if the measured value of the first magnetic field sensor (410) exceeds an MR-typical threshold, for example 100 mT, the evaluation of the second magnetic field sensor (440) may be omitted.

In one or more embodiments, the second magnetic field sensor (440) may be integrated in the electrode line, such as using one or more of a reed switch, a GMR sensor or the like, and the second magnetic field sensor (440) may function with a fixed threshold (for example 5 mT). In at least one embodiment, the MR environment may then be confirmed (for example a field >1 mT) or rejected (for example a field <1 mT) upon activation of the electrode sensor, such as the second magnetic field sensor (440) integrated in the electrode line, via the implant sensor, such as the first magnetic field sensor (410).

It will be apparent to those skilled in the art that numerous modifications and variations of the described examples and embodiments are possible in light of the above teaching. The disclosed examples and embodiments are presented for purposes of illustration only. Other alternate embodiments may include some or all of the features disclosed herein. Therefore, it is the intent to cover all such modifications and alternate embodiments as may come within the true scope of this invention.

What is claimed is:

1. An implantable medical device (IMD) comprising:
   at least one power supply;
   one or more of at least one sensing device and at least one stimulation device,
   at least one control unit;
   at least one magnetic resonance (MR) detection unit; and
   at least two magnetic field sensors that detect magnetic field strengths comprising at least a first magnetic field sensor and a second magnetic field sensor;
   wherein the at least one power supply is connected directly or indirectly to one or more of the at least one sensing device, the at least one stimulation device, the at least one control unit, the at least one MR detection unit and the at least two magnetic field sensors, and
   wherein the at least one control unit is connected directly or indirectly to one or more of the at least one sensing device and the at least one stimulation device, and,
   wherein the at least one control unit is connected directly or indirectly to the at least one MR detection unit and the at least two magnetic field sensors; wherein the at least two magnetic field sensors are arranged spatially separately from one another and transmit the magnetic field strengths to the at least one MR detection unit; and,
   wherein the at least one MR detection unit
      determines one or more of a spatial and a temporal gradient of the magnetic field strengths from the magnetic field strengths detected by the at least two magnetic field sensors and transmitted to the at least one MR detection unit,
      detects an MR field, and,
      transmits an MR signal to the at least one control unit if either
         at least one magnetic field strength of the magnetic field strengths detected by the at least two magnetic field sensors is above a first predetermined threshold value, or the magnetic field strengths detected by the at least two magnetic field sensors are below the first predetermined threshold value and above a second predetermined threshold value, and one or more of the spatial and the temporal gradients of the magnetic field strengths lie in a first predetermined range of threshold values;
         wherein when the first magnetic field sensor senses the at least one magnetic field strength above the first predetermined threshold value, the second magnetic field sensor is queried and evaluated to determine if the second magnetic field sensor senses the at least one magnetic field strength above the first predetermined threshold.

2. The IMD as claimed in claim 1, wherein the at least one control unit changes into a predetermined operating mode in response to the MR signal of the at least one MR detection unit.

3. The IMD as claimed in claim 2, wherein the predetermined operating mode includes parameters that are predetermined in accordance with one or more of the magnetic field strengths detected by the at least one MR detection unit, the temporal gradient fields and the spatial gradient fields.

4. The IMD as claimed in claim 1, wherein the at least one MR detection unit evaluates a gradient and an absolute value of the detected magnetic field strengths when the detected magnetic field strengths lie below the first predetermined threshold value.

5. The IMD as claimed in claim 1, wherein the at least two magnetic field sensors are arranged within the IMD, or at least one magnetic field sensor of the at least two magnetic field sensors is arranged within the IMD and at least one further magnetic field sensor of the at least two magnetic field sensors is arranged in an electrode line connected to the IMD.

6. The IMD as claimed in claim 1, wherein a minimum distance between the at least two magnetic field sensors is selected in accordance with a resolution of the at least two magnetic field sensors, such that the resolution is sufficient to distinguish between a local magnetic field and a widely distributed MR field with reference to the spatial gradient fields.

7. The IMD as claimed in claim 1, wherein when an MR signal is transmitted to the at least one control unit, the at least one control unit causes at least one predetermined automatic switchover of at least one implant setting of said IMD.

8. The IMD as claimed in claim 1, further comprising one or more of at least one elongate electrode line and a sensor line.

9. The IMD as claimed in claim 1, wherein the at least one MR detection unit identifies an MR-typical journey of an IMD on a patient bed, based on one or more of a change over time of measured values of the at least two magnetic field sensors and a difference between the measured values of the at least two magnetic field sensors.

* * * * *